US00PP08843P

United States Patent [19]

VandenBerg

[11] Patent Number: Plant 8,843

[45] Date of Patent: Jul. 19, 1994

[54] CHRYSANTHEMUM PLANT NAMED PHOENIX

[75] Inventor: Cornelis P. VandenBerg, Salinas, Calif.

[73] Assignee: Yoder Brothers, Inc., Barberton, Ohio

[21] Appl. No.: 99,657

[22] Filed: Jul. 30, 1993

[51] Int. Cl.[5] ..... A01H 5/00

[52] U.S. Cl. ..... Plt./78

[58] Field of Search ..... Plt. 78, 76, 82.2

*Primary Examiner*—Howard J. Locker

*Attorney, Agent, or Firm*—Foley & Lardner

[57] ABSTRACT

A Chrysantheum plane named Phoenix particularly characterized by its flat capitulum form; quilled decorative capitulum type; soft apricot-ivory flower color with slightly darker center of the flower; diameter across face of capitulum of 114 to 140 mm when fully opened, when grown as a pinched disbudded pot mum; photoperiodic flowering response to short days of 50 to 57 days; plant height, with 21 to 24 long days after sticking unrooted cuttings, and with 1 application of 2500 ppm B-9 SP, ranges from 23 to 33 cm when grown as a pinched pot mum with 4 cuttings in a 15 cm pot; branching pattern is spreading, each plant having 4 to 5 laterals after pinch; and recommended as disbud pot mum.

3 Drawing Sheets

The present invention comprises a new and distinct cultivar of Chrysanthemum, botanically known as *Dendranthema grandiflora,* and referred to by the cultivar name Phoenix.

Phoenix, identified as 5906 (90-728005), was originated from a cross made by Cornelis P. VandenBerg in a controlled breeding program in Salinas, Calif., in 1990.

The female parent of Phoenix was the cultivar identified as SURF, disclosed in U.S. Plant Pat. No. 4,585.

The male parent of Phoenix was an unnamed seedling identified as 6597 (86-379001), and described as a spooned decorative disbud pot mum with a yellow ray floret color; a flowering response to short days of 52 to 57 days under normal conditions in Salinas, Calif.; a plant height of 23 to 36 cm with 16 to 23 long days after sticking unrooted cuttings prior to start of short days and 1 to 2 applications of 2500 ppm B-9 SP when grown as a pinched pot mum; branching habit of 3 to 5 laterals developing after pinch; and diameter of capitulum of 114 to 130 mm.

Phoenix was discovered and selected as one flowering plant within the progeny of the stated cross by Cornelis P. VandenBerg in December 1990, in a controlled environment in Salinas, Calif.

The first act of asexual reproduction of Phoenix was accomplished when vegetative cuttings were taken from the initial selection in March 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Phoenix are firmly fixed and are retained through successive generations of asexual reproduction.

Phoenix has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Phoenix, which, in combination, distinguish this Chrysanthemum as a new and distinct cultivar.

1. Flat capitulum form.
2. Quilled decorative capitulum type.
3. Soft apricot-ivory flower color with slightly darker center of the flower.
4. Diameter across face of capitulum of 114 to 140 mm when fully opened, when grown as a pinched disbudded pot mum.
5. Photoperiodic flowering response to short days of 50 to 57 days.
6. Plant height, with 21 to 24 long days after sticking unrooted cuttings and with 1 application of 2500 ppm B-9 SP, ranges from 23 to 33 cm when grown as a pinched pot mum with 4 cuttings in a 15 cm pot.
7. Branching pattern is spreading, each plant having 4 to 5 laterals after pinch.
8. Recommended as disbud pot mum.

The accompanying photographic drawings show typical inflorescence and leaf characteristics of Phoenix, with the colors being as nearly true as possible with illustrations of this type.

Sheet 1 is a color photograph of Phoenix grown as a pinched disbudded pot mum with 4 cuttings in a 15 cm pot.

Sheet 2 is a black and white photograph of three views of the inflorescence of Phoenix.

Sheet 3 is a black and white photograph showing the upper and under sides of the leaves of Phoenix at 3 stages of development (mature, intermediate and immature).

In sheets 2 and 3 a measuring tape in centimeters has been added.

The combination of soft apricot-ivory flower color with a slightly darker center of the flower, and the quilled decorative capitulum type is not represented in any of the commercial cultivars known to the inventor.

Therefore, no comparison is made with existing commercial varieties.

In the following description color references are made to The Royal Horticultural Society Colour Chart. The color values were determined on plant material grown as a pinched disbudded pot mum in Salinas, Calif. on Oct. 26, 1992.

Classification:

*Botanical.*—*Dendranthema grandiflora* cv. Phoenix.

*Commercial.*—Quilled decorative disbud pot mum.

INFLORESCENCE

A. Capitulum:

*Form.*—Flat.

*Type.*—Quilled decorative.

*Diameter across face.*—114 to 140 mm when fully opened when grown as a pinched disbudded pot mum.

B. Corolla of ray florets:

*Color (general tonality from a distance of three meters).*—Soft apricot-ivory.

*Color (outer surface).*—Between 11D and 13D. Immature flowers and center of mature flowers closest to 20C to 20D.

*Color (inner surface).*—11D.

*Shape.*—Straight, quilled.

C. Corolla of disc florets:

*Color (mature).*—14B.

*Color (immature).*—144A to 144B.

D. Reproductive organs:

*Androecium.*—Present on disc florets only; scant pollen.

*Gynoecium.*—Present on both ray and disc florets.

PLANT

A. General appearance:

*Height.*—23 to 33 cm when grown as a pinched pot mum in a 15 cm pot with 21 to 24 long days after direct sticking of unrooted cuttings and 1 application of 2500 ppm B-9 SP.

*Branching pattern.*—Spreading, with 4 to 5 laterals after pinch.

B. Foliage:

*Color (upper surface).*—147A.

*Color (under surface).*—147B.

*Shape.*—See photograph.

I claim:

1. A new and distinct Chrysanthemum plant named Phoenix, as described and illustrated.

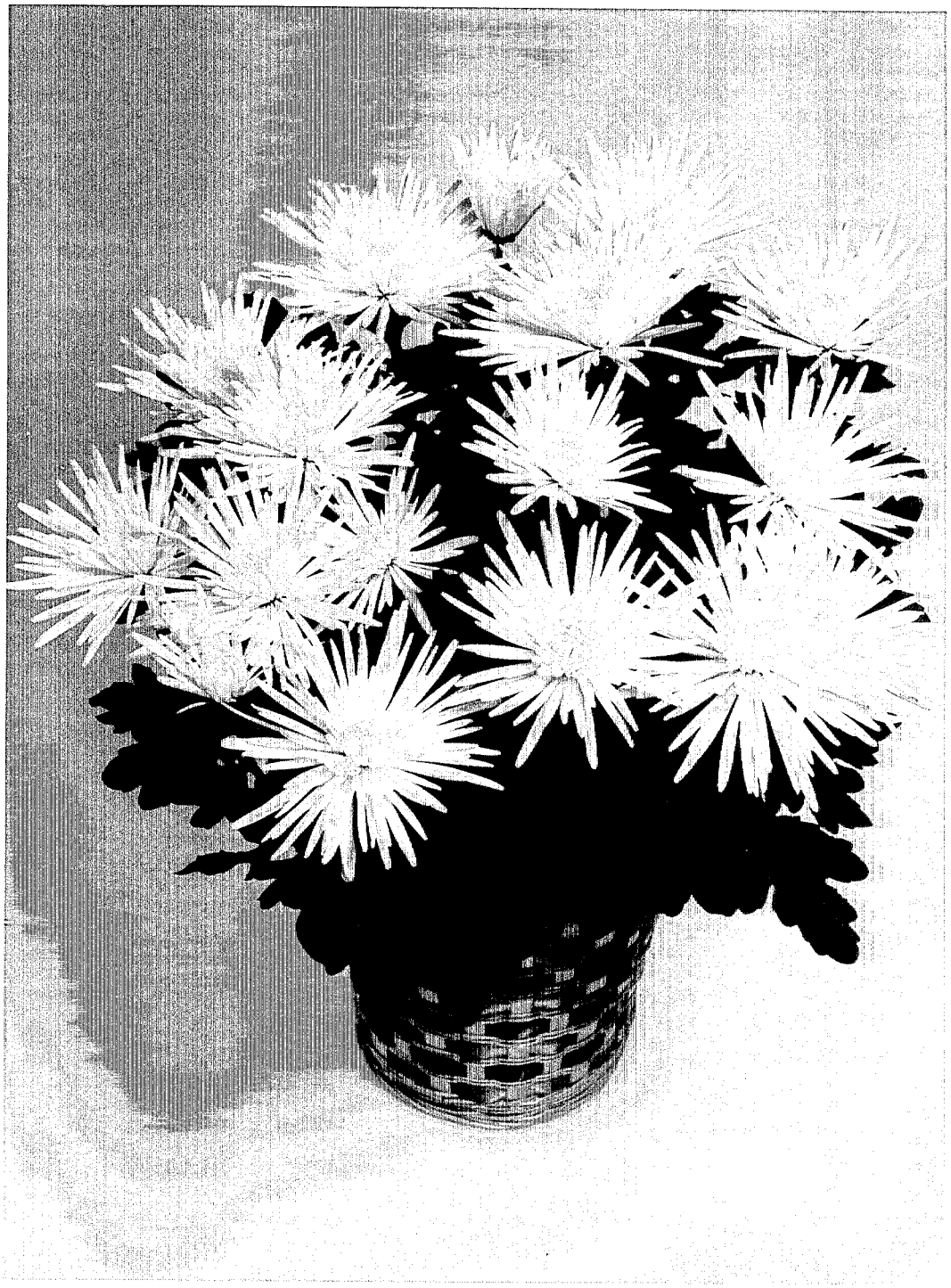

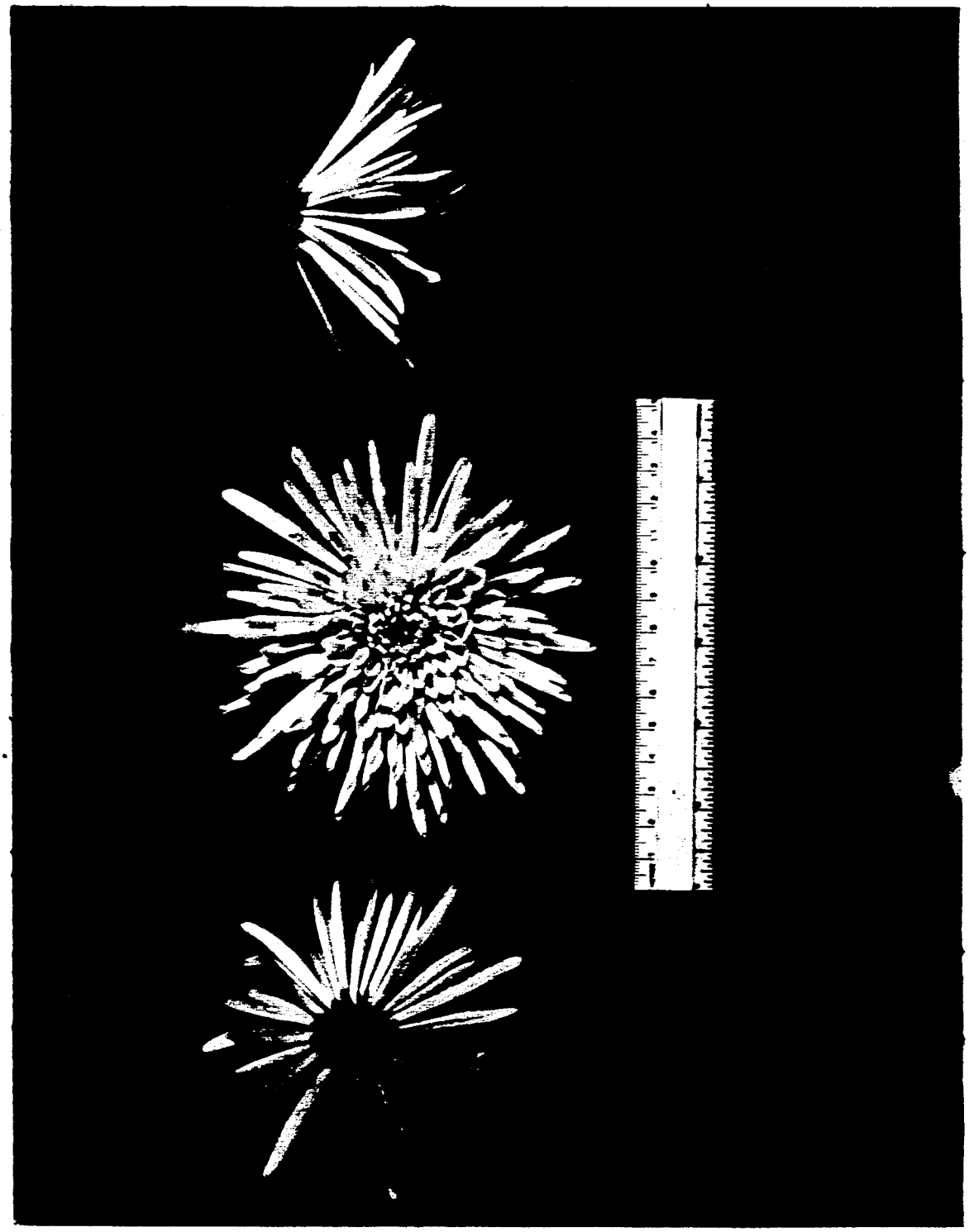

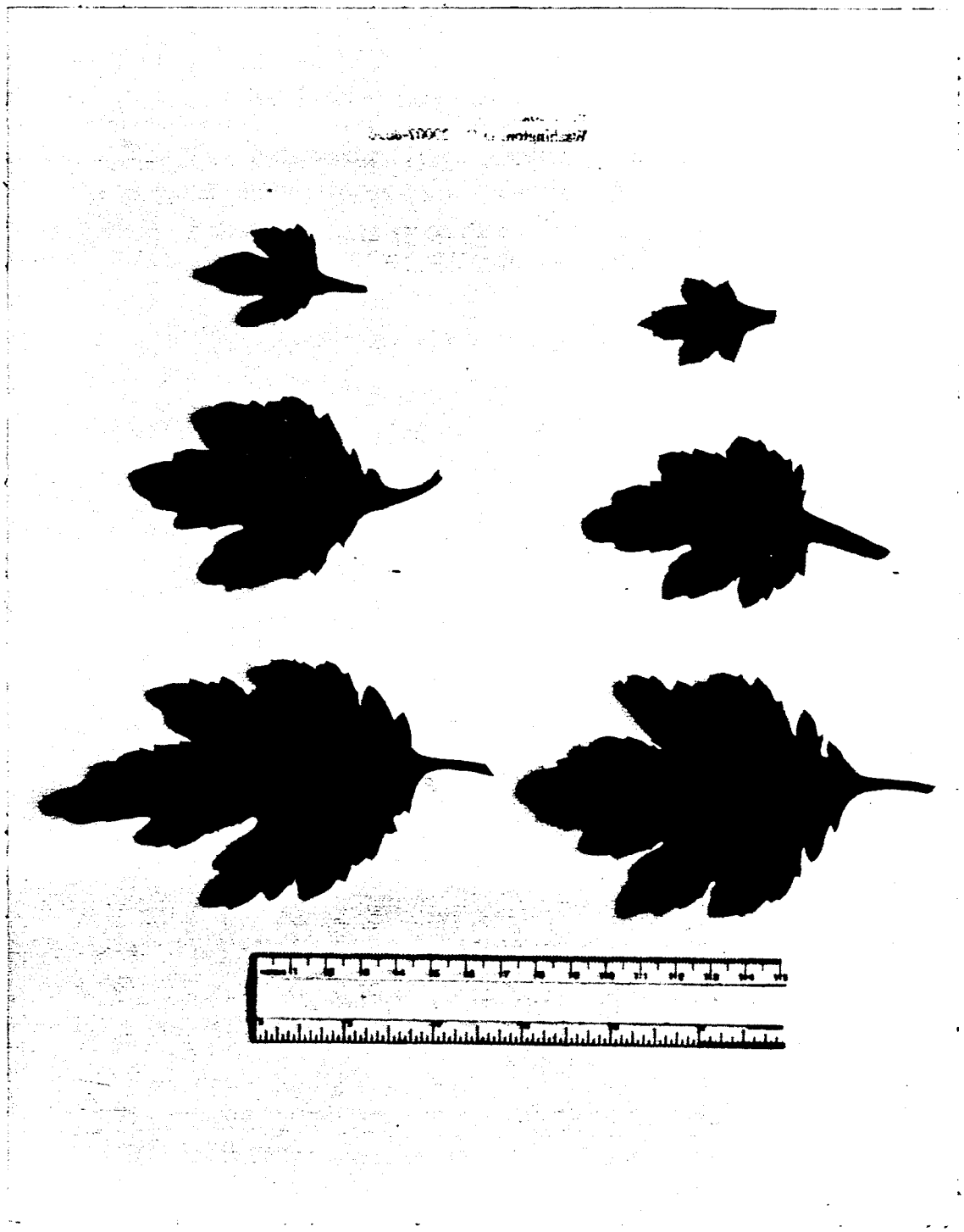

* * * * *